United States Patent [19]

Canas Poblet et al.

[11] Patent Number: 5,739,272
[45] Date of Patent: Apr. 14, 1998

[54] PROCEDURE FOR OBTAINING CARBOCALCITONIN

[75] Inventors: Marcos Canas Poblet; Berta Ponsati Obiols; Gemma Jodas Farres; David Andreu Martinez, all of Barcelona, Spain

[73] Assignee: Lipotec, S.A., Barcelona, Spain

[21] Appl. No.: 193,755

[22] Filed: Feb. 3, 1994

[30] Foreign Application Priority Data

Feb. 3, 1993 [ES] Spain ................................ 9300197

[51] Int. Cl.$^6$ .......................... A61K 38/23; C07K 14/585
[52] U.S. Cl. ........................ 530/307; 530/326; 530/327; 525/54.1
[58] Field of Search ........................ 530/307, 326–327; 525/54.1

[56] References Cited

U.S. PATENT DOCUMENTS

| | | |
|---|---|---|
| 4,804,742 | 2/1989 | Neiss et al. |
| 4,908,475 | 3/1990 | Callahan et al. |

FOREIGN PATENT DOCUMENTS

| | | |
|---|---|---|
| 0518295A2 | 8/1992 | European Pat. Off. |
| 2616399 | 11/1976 | Germany |
| 0258490 | 10/1988 | Japan |
| 12809 | 11/1990 | WIPO |
| 19643 | 6/1992 | WIPO |

OTHER PUBLICATIONS

Experientia, vol.32, No. 9, 1976, pp. 1104–1106, T.Morikawa et al. "Synthesis of Eel–Calcitonia . . . Contribution of the Disulfide Bond to the Hormonal Activity".
Chemical Abstracts, vol. 114, No. 11, Mar. 18, 1991, Columbus, Ohio, US; Abstract No. 102741, Belschaw et al. "Chlorotrimehtylsilane medicated formation of omega–allyl esters of aspartic glutamic acids", p. 822, col. L; Abstract; SYNTH.COMMUN, vol. 20, No. 20, 1990, pp.3157–3160.
Barany et al. Int. J. Peptide Protein Res. vol. 30 p. 705 (1987).
Atherton et al, J. Am. Chem Soc. vol. 97 p. 6584 (1975).
Alberico et al. J. Org. Chem vol. 55 p. 3730 (1990).
Fields et al. Int. J. Peptide Protein Res vol. 35 pp. 161–214 (1990).

Sigma Catalog (1993) pp. 82–86.

Primary Examiner—Anthony C. Caputa
Assistant Examiner—Benet Prickril
Attorney, Agent, or Firm—Wigman, Cohen, Leitner & Myers, P.C.

[57] ABSTRACT

A procedure for obtaining carbocalcitonin comprising the condensation of fragment 1, a docosapeptide corresponding to the carboxamide end of the carbocalcitonin sequence, conveniently protected and anchored on resin, with fragment 2 or 3, a nonapeptide corresponding to the amino end of the salmon calcitonin sequence, with a ready-formed cycle between the Asu and Ser residua, and the treatment of the complete peptide skeleton (fragment 6 or 7) with an acid to free the totally deprotected peptide from the resin.

H—Lys(Boc)—Leu—Ser(tBu)—Gln—Glu(OtBu)—Leu—His(Trt)—

Lys(Boc)—Leu—Gln—Thr(tBu)—Tyr(tBu)—Pro—Arg(Pmc)—

Thr(tBu)—AA'$_{25}$—AA'$_{26}$—Gly—AA'$_{28}$—Gly—Thr(tBu)—Pro—Ⓡ

Fragment 1 (SEQ. ID NO: 1)

Ser(X)—Asn—Leu—Ser(X)—Thr(X)—Asu—Val—Leu—Gly—OH
   |                              |
HNCO——————————————(CH$_2$)$_5$

X = H ——▶ Fragment 2 (SEQ. ID NO: 4)

X = tBu ——▶ Fragment 3 (SEQ. ID NO: 4)

Ser(X)—Asn—Leu—Ser(X)—Thr(X)—Asu—Val—Leu—Gly—
   |                              |
HNCO——————————————(CH$_2$)$_5$

Lys(Boc)—Leu—Ser(tBu)—Gln—Glu(OtBu)—

Leu—His(Trt)—Lys(Boc)

Leu—Gln—Thr(tBu)—Tyr(tBu)—Pro—Arg(Pmc)—Thr(tBu)—

AA'$_{25}$—AA'$_{26}$—Gly—AA'$_{28}$—Gly—Thr(tBu)—Pro—Ⓡ

X = H ——▶ Fragment 6 (SEQ. ID NO: 5)

X = tBu ——▶ Fragment 7 (SEQ. ID NO: 5)

26 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 22 amino acids
      ( B ) TYPE: amino acid
      ( C ) TOPOLOGY: linear ( i i ) MOLECULE TYPE: peptide ( v ) FRAGMENT TYPE: C-Terminal type ( i x ) FEATURE:
      ( D ) OTHER INFORMATION:
         Lys at position 1 substituted with
         t- butoxycarbonyl
         Ser at position 3 substituted with
         tert- butyl
         Glu at position 5 substituted with
         tert- butyl
         His at position 7 substituted with trityl
         Lys at position 8 substituted with
         t- butoxycarbonyl
         Thr at position 11 substituted with
         tert- butyl
         Tyr at position 12 substituted with
         tert- butyl
         Arg at position 14 substituted with
         2,2,5,7,8- pentamethylchroman-6-sulphonyl
         Thr at position 15 substituted with
         tert- butyl
         Xaa at position 16 being Asn or Asp
         substituted with tert-butyl
         Xaa at position 17 being Val or Thr
         substituted with tert-butyl
         Xaa at position 19 being Ala or Ser
         substituted tert-butyl
         Thr at position 21 substituted with
         tert- butyl
         Pro at position 22 is attached to a
         polymer bead.

( x i ) SEQUENCE DESCRIPTION: SEQ ID NO:1:

Lys  Leu  Ser  Gln  Glu  Leu  His  Lys  Leu  Gln  Thr  Tyr  Pro  Arg  Thr  Xaa
1                  5                        10                       15

Xaa  Gly  Xaa  Gly  Thr  Pro
            20

( 2 ) INFORMATION FOR SEQ ID NO:2:

( i ) SEQUENCE CHARACTERISTICS:
      ( A ) LENGTH: 31 amino acids
      ( B ) TYPE: amino acid
      ( D ) TOPOLOGY: linear ( i i ) MOLECULE TYPE: peptide ( i x ) FEATURE:
      ( D ) OTHER INFORMATION: (Corresponds to the amino
         acid sequence of Fragments 9 and 10):
         Ser at position 1 substituted with
         9- fluorenylmethoxy carbonyl and
         substituted with tert-butyl (Fragment 10)
         Ser at position 4 substituted with tert-butyl
         Thr at position 5 substituted with tert-butyl
         Xaa at position 6 being L-'-aminosuberic acid
         substituted with O-allyl
         Lys at position 10 substituted with t-butoxy carbonyl
         Ser at position 12 substituted with tert-butyl
         Glu at position 14 substituted with tert-butyl His at position 16 substituted with trityl
Lys at position 17 substituted with t-butoxy carbonyl
Thr at position 20 substituted with tert-butyl
Tyr at position 21 substituted with tert-butyl
Arg at position 23 substituted with 2,2,5,7,8
pentamethychroman-6-sulphonyl
Thr at position 24 substituted with tert-butyl
Xaa at position 25 is Asn or Asp substituted
with tert- butyl
Xaa at position 26 is Val or Thr substituted
with tert- butyl
Xaa at position 28 is Ala or Ser protected
by tert- butyl
Thr at position 30 is substituted with tert-butyl
Pro at position 31 is attached to the solid support ( x i ) SEQUENCE DESCRIPTION: SEQ ID NO: 2:

Ser Asn Leu Ser Thr Xaa Val Leu Gly Lys Leu Ser Gln Glu Leu
1               5                   10                  15

His Lys Leu Gln Thr Tyr Pro Arg Thr Xaa Xaa Gly Xaa Gly Thr Pro
                20                  25              30

( 2 ) INFORMATION FOR SEQ ID NO:3:

( i ) SEQUENCE CHARACTERISTICS:
    ( A ) LENGTH:9 amino acids
    ( B ) TYPE:amino acid
    ( D ) TOPOLOGY:linear ( i i ) MOLECULE TYPE:peptide ( i x ) FEATURE:C-Terminal
    ( D ) OTHER INFORMATION: (Corresponds to amino
            acid sequence in Fragments 4 and 5)
            Ser at position 1 is derivatized with
            9- fluorenylmethoxycarbonyl (Fragments 4 and 5)
            and tert- butyl (Fragment 5)
            Ser at position 4 is derivatized with tert-butyl
            Thr at position 5 is derivatized with tert-butyl
            Xaa at position 6 being L-'-aminosuberic acid
            is derivatized with O-allyl
            Gly at position 9 is attached to a Wang-type
            polymer bead ( x i ) SEQUENCE DESCRIPTION: SEQ ID NO:3:

Ser Asn Leu Ser Thr Xaa Val Leu Gly
1               5

( 2 ) INFORMATION FOR SEQ ID NO:4:

( i ) SEQUENCE CHARACTERISTICS:
    ( A ) LENGTH:9 amino acids
    ( B ) TYPE:amino acid
    ( D ) TOPOLOGY:linear ( i i ) MOLECULE TYPE:peptide ( i x ) FEATURE:C-Terminal
    ( D ) OTHER INFORMATION: (Corresponds to amino
            acid sequence in Fragments 2 and 3)
            Ser at position 1 is cyclized with
            the omega carboxcylic acid of aminosuberic
            acid of position 6
            Ser at position 4 is derivatized with tert-butyl
            Thr at position 5 is derivatized with tert-butyl
            Xaa at position 6 being L-'-aminosurebic acid
            Gly at position 9 is attached to a Wang-type
            polymer bead ( x i ) SEQUENCE DESCRIPTION: SEQ ID NO:4:

Ser Asn Leu Ser Thr Xaa Val Leu Gly
1               5

( 2 ) INFORMATION FOR SEQ ID NO:5:

( i ) SEQUENCE CHARACTERISTICS:
        ( A ) LENGTH:31 amino acids
        ( B ) TYPE:amino acid
        ( D ) TOPOLOGY:linear ( i i ) MOLECULE TYPE:peptide ( i x ) FEATURE:
        ( D ) OTHER INFORMATION: (Corresponds to the amino
            acid sequence of Fragments 6 and 7):
            Ser at position 1 is cyclized with the
            omega carboxcylic acid of aminosuberic
            acid of position 6 and substituted with
            tert-butyl (Fragment 7)
            Ser at position 4 substituted with tert-butyl
            Thr at position 5 substituted with tert-butyl
            Xaa at position 6 being L-'-aminosuberic acid
            Lys at position 10 substituted with t-butoxy carbonyl
            Ser at position 12 substituted with tert-butyl
            Glu at position 14 substituted with tert-butyl
            His at position 16 substituted with trityl
            Lys at position 17 substituted with t-butoxy carbonyl
            Thr at position 20 substituted with tert-butyl
            Tyr at position 21 substituted with tert-butyl
            Arg at position 23 substituted with 2,2,5,7,8
            pentamethychroman-6-sulphonyl
            Thr at position 24 substituted with tert-butyl
            Xaa at position 25 is Asn or Asp substituted
            with tert- butyl
            Xaa at position 26 is Val or Thr substituted
            with tert- butyl
            Xaa at position 28 is Ala or Ser protected
            by tert- butyl
            Thr at position 30 is substituted with tert-butyl
            Pro at position 31 is attached to the solid support ( x i ) SEQUENCE DESCRIPTION: SEQ ID NO: 5:

Ser Asn Leu Ser Thr Xaa Val Leu Gly Lys Leu Ser Gln Glu Leu
1               5                   10                  15

His Lys Leu Gln Thr Tyr Pro Arg Thr Xaa Xaa Gly Xaa Gly Thr Pro
                20                  25                  30

( 2 ) INFORMATION FOR SEQ ID NO:6:

( i ) SEQUENCE CHARACTERISTICS:
        ( A ) LENGTH:31 amino acids
        ( B ) TYPE:amino acid
        ( D ) TOPOLOGY:linear ( i i ) MOLECULE TYPE:peptide ( i x ) FEATURE:
        ( D ) OTHER INFORMATION: (Corresponds to the amino
            acid sequence of carbocalcitonin):
            Ser at position 1 is cyclized with the
            omega carboxcylic acid of aminosuberic
            acid of position 6
            Xaa at position 6 being L-'-aminosuberic acid
            Xaa at position 25 is Asn or Asp
            Xaa at position 26 is Val or Thr
            Xaa at position 28 is Ala or Ser
            Pro at position 31 is carboxylamide ( x i ) SEQUENCE DESCRIPTION: SEQ ID NO: 6:

Ser Asn Leu Ser Thr Xaa Val Leu Gly Lys Leu Ser Gln Glu Leu
1               5                   10                  15

His Lys Leu Gln Thr Tyr Pro Arg Thr Xaa Xaa Gly Xaa Gly Thr Pro
                20                  25                  30

( 2 ) INFORMATION FOR SEQ ID NO:7:

( i ) SEQUENCE CHARACTERISTICS:

( A ) LENGTH:10 amino acids
        ( B ) TYPE:amino acid
        ( D ) TOPOLOGY:linear ( i i ) MOLECULE TYPE:peptide ( i x ) FEATURE:C-Terminal
        ( D ) OTHER INFORMATION:
            Ser at position 1 is derivatized with
            9- fluorenylmethoxycarbonyl tert-butyl
            Ser at position 4 is derivatized with tert-butyl
            Thr at position 5 is derivatized with tert-butyl
            Xaa at position 6 being L-'-aminosuberic acid
            is derivatized with O-allyl
            Gly at position 9 is substituted with Riniker handle
            Ile at position 10 is derivatized with para-methyl
            benzhydrilamine ( x i ) SEQUENCE DESCRIPTION: SEQ ID NO:7:

Ser Asn Leu Ser Thr Xaa Val Leu Gly Ile
 1             5                    10

( 2 ) INFORMATION FOR SEQ ID NO:8:

( i ) SEQUENCE CHARACTERISTICS:
        ( A ) LENGTH:23 amino acids
        ( B ) TYPE:amino acid
        ( C ) TOPOLOGY:linear ( i i ) MOLECULE TYPE:peptide ( v ) FRAGMENT TYPE:C-Terminal type ( i x ) FEATURE:
        ( D ) OTHER INFORMATION:
            Lys at position 1 substituted with
            t- butoxycarbonyl
            Ser at position 3 substituted with
            tert- butyl
            Glu at position 5 substituted with
            tert- butyl
            His at position 7 substituted with trityl
            Lys at position 8 substituted with
            t- butoxycarbonyl
            Thr at position 11 substituted with
            tert- butyl
            Tyr at position 12 substituted with
            tert- butyl
            Arg at position 14 substituted with
            2,2,5,7,8- pentamethylchroman-6-sulphonyl
            Thr at position 15 substituted with
            tert- butyl
            Xaa at position 16 being Asn or Asp
            substituted with tert-butyl
            Xaa at position 17 being Val or Thr
            substituted with tert-butyl
            Xaa at position 19 being Ala or Ser
            substituted tert-butyl
            Thr at position 21 substituted with
            tert- butyl
            Pro at position 22 is substituted with
            p-[(R,S)- 2,4-dimethoxybenzyl]-phenoxyacetic acid
            Ile at position 23 is substituted with
            para- methylbenzhydrilamine ( x i ) SEQUENCE DESCRIPTION: SEQ ID NO:8:

Lys Leu Ser Gln Glu Leu His Lys Leu Gln Thr Tyr Pro Arg Thr Xaa
 1             5                    10                   15

Xaa Gly Xaa Gly Thr Pro Ile
           20

PROCEDURE FOR OBTAINING CARBOCALCITONIN

The present invention relates to a procedure for solid phase preparation of salmon and eel carbocalcitonin and all of its pharmaceutically acceptable salts formed by acid addition or complexes thereof. The invention further relates to the preparation of intermediate compounds which are useful in the synthesis of carbocalcitonin according to the invention, in particular the preparation of two aminosuberic acid derivatives, not previously described, the w-allyl ester of aminosuberic acid and the w-allyl ester of N-α-9-fluorenylmethoxycarbonyl-aminosuberic acid.

BACKGROUND OF THE INVENTION

The carbocalcitonins are unnatural peptides which are analogous to the calcitonins but which are very much more active. Like the calcitonins carbocalcitonins have important therapeutic applications for the treatment of hypercalcemia, osteoporosis or Paget's disease by virtue of its ability to regulate the level of calcium in the blood. These compounds have greater stability in serum, the liver or the kidneys than natural calcitonins and are more stable during the process of purification and in storage due to the absence of the disulphide bridge which is present in the calcitonins.

Naturally occurring calcitonins, such as those of eel, salmon or humans, are polypeptides of 32 amino acids, the residue 1 and 7 being L-cysteine, whose side chains are linked to form a disulphide bridge. Carbocalcitonins do not have L-cysteine in said positions, position 7 being occupied instead by L-α-aminosuberic acid (Asu) with the formula:

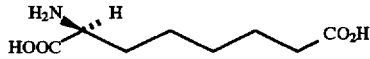

the w-carboxyl group of which is linked to the terminal amino group of the peptide to produce a cyclic structure.

In order to generate the cycle between the Asu side chain and the terminal amino end in a selective way which avoids secondary reactions, the Asu side chain must be protected with a group which is orthogonal to the rest and to the peptide-resin link. The present invention describes a procedure for obtaining the new aminosuberic acid derivative with the, side chain protected with the allyl group and the α-amino protected by means of Fmoc.

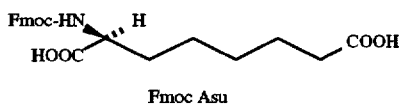

Fmoc Asu

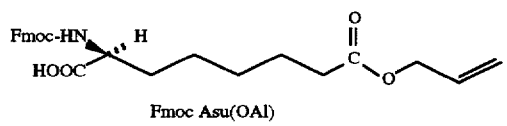

Fmoc Asu(OAl)

This protective group is eliminated by means of palladium catalysis and is totally orthogonal to the other protective groups and the peptide-resin link (Greene T. W. Protective Group in Organic Synthesis, Wiley, N.Y., 1981, p.169).

BRIEF DESCRIPTION OF THE TABLES

Tables 1–4 diagram the procedure for obtaining a carbocalcitonin based on solid phase synthesis according to the process of the present invention. The "Fragments" identified in the Tables correspond to the amino acid sequences as follows:

(Fragment 1=SEQ. ID NO: 1; Fragments 2 and 3=SEQ. ID NO: 4; Fragments 4 and 5=SEQ. ID NO: 3; Fragments 6 and 7=SEQ ID NO: 5; Fragments 9 and 10=SEQ. ID NO: 2; and Carbocalcitonin=SEQ. ID NO: 6.)

If, however, a discrepancy were to exist between the fragments shown in the tables and specification and the Sequence Listing, due to typographical error, the fragments shown in the tables and specification are deemed to constitute the invention.

Furthermore the invention describes a procedure (Table 1) for obtaining carbocalcitonin using said Asu derivative, in particular for obtaining the analogues of salmon and eel calcitonin, the formula (SEQ. ID NO: 6) of which is expressed as follows:

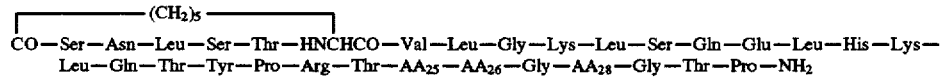

where $AA_{25}$ is Asp or Asn, $AA_{26}$ is Val or Thr and $AA_{28}$ is Ala or Ser.

More particularly, the present invention provides a procedure for obtaining carbocalcitonin based on the solid phase synthesis using Fmoc/tBu type protective group methodology (with convenient functionalized supports) combined with a convergent strategy, all according to the following (Table 1):

TABLE 1
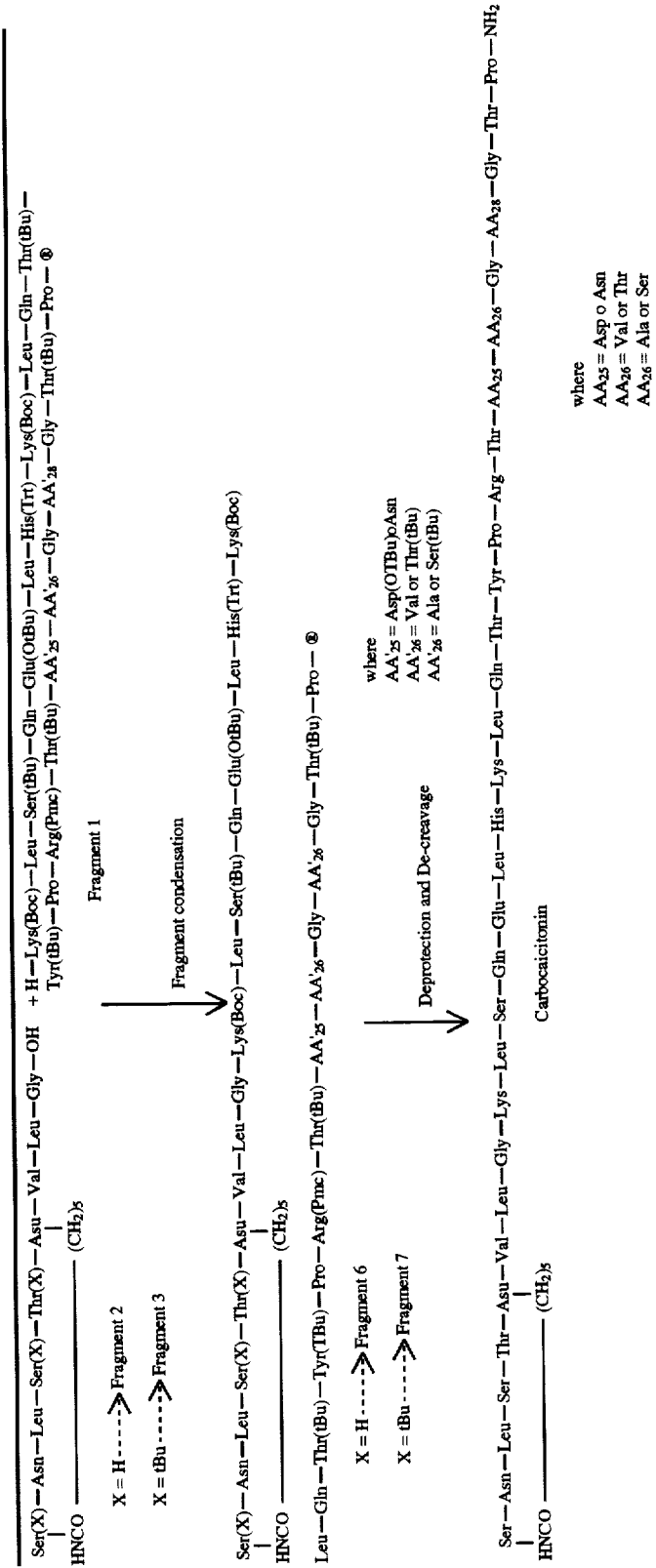

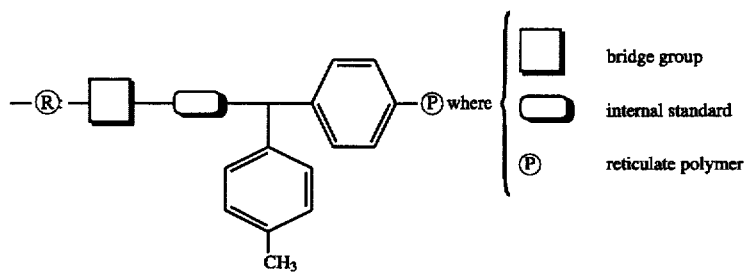

As shown, ⓡ refers to the ⓡ of Table 1, namely the solid support, internal standard and bridge group having the structure shown after the colon.

Referring to FIG. 1 above, the procedure of this invention consists of the condensation of fragment 1 (SEQ ID NO:1), a docosapeptide corresponding to the carboxamide end of the carbocalcitonin sequence, conveniently protected and anchored on resin, with fragment 2 (SEQ. ID NO:4), a nonapeptide corresponding to the amino end of the carbocalcitonin sequence, with the cycle already formed between the $Asu^9$ and $Ser^1$ residues, to obtain fragment 6 (SEQ. ID NO:5). Another option consists of coupling fragment 3 (SEQ. ID NO:4), which is also cyclic, to fragment 1 (SEQ. ID NO:1), thereby obtaining fragment 7 (SEQ. ID NO:5), all according to what is shown in Table 1.

Once the complete peptide skeleton (fragment 6 or 7) (SEQ. ID NO:5) has been constructed the peptide is liberated from the resin and totally deprotected, already in its cyclic form, by means of an acid treatment. Finally, after subsequent purification, chemically pure carbocalcitonin is obtained.

In particular, the condensation of fragment 1 (SEQ. ID NO:1) with fragment 2 or 3 (SEQ. ID NO:4) (Table 1) which leads to fragment 6 or 7 (SEQ. ID NO:5) is carried out by the conventional methods of solid phase synthesis which have already been described. Once condensation is complete, the peptide-resin is subjected to a simultaneous process of deprotection of the side chains and de-anchoring the resin using trifluoroacetic acid in the presence of carbocation sequestering agents. The resulting crude is purified by high pressure liquid chromatography and ion exchange chromatography. The collection of homogeneous fractions is combined and freeze-dried, dried, thereby obtaining carbocalcitonin In the free state.

According to another modality, the procedure of the invention may be carried out according to the following Table 2:

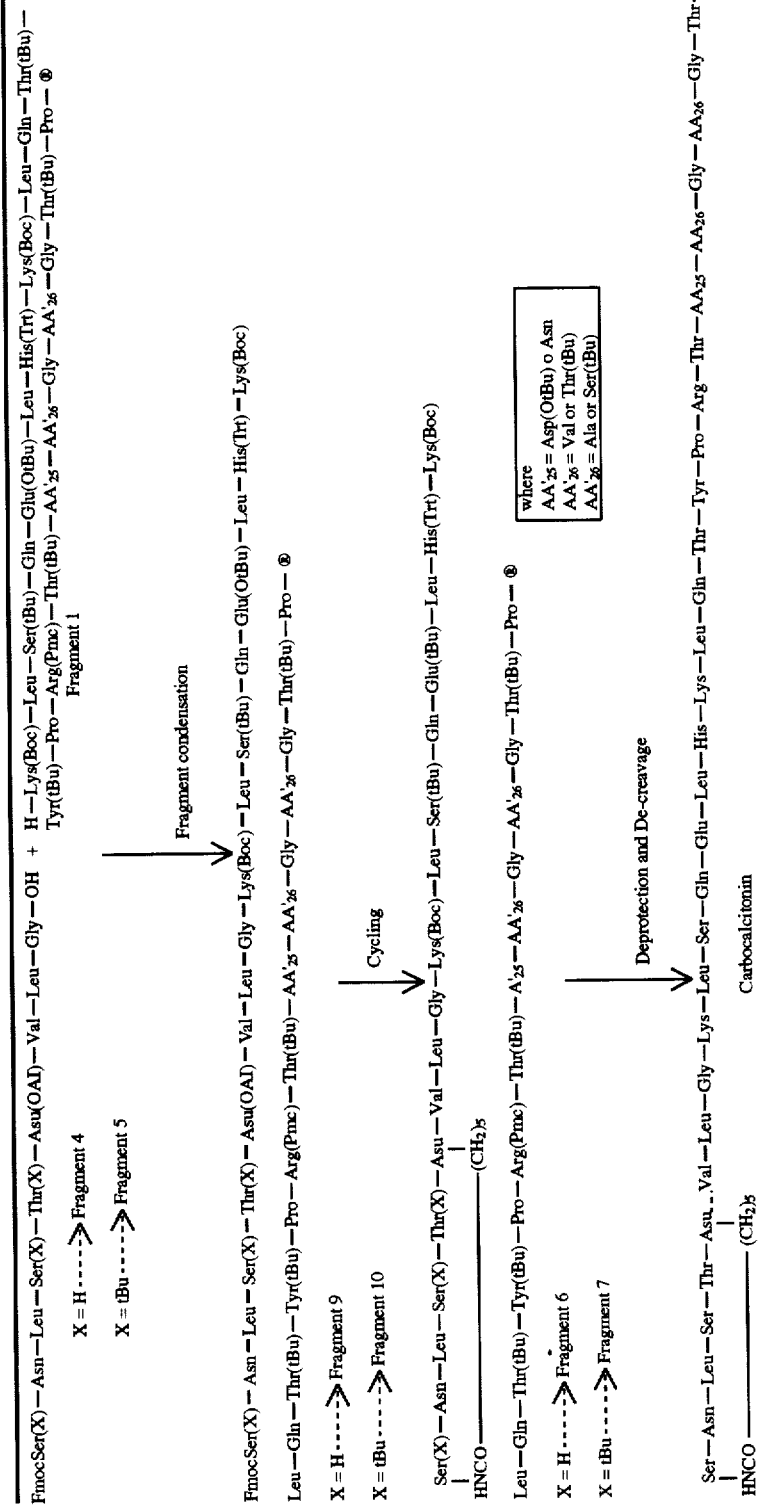

where R is defined as before.

According to Table 2, the cycling can also be carried out after condensation. To do this there two possibilities: condense fragment 1 SEQ. ID NO:1, corresponding to the docosapeptide, with fragment 4 (SEQ. ID NO:3) to obtain fragment 9 (SEQ. ID NO:2), or condense fragment 5 (SEQ. ID NO:3) to obtain 10 (SEQ. ID NO:2), as shown in Table 2. Alternatively, fragment 10 (SEQ. ID NO:2) can be obtained by means of linear synthesis, i.e. by incorporating one amino acid residuum after another until sequence is complete, as shown is Table 3.

Once the skeleton corresponding to fragments 9 or 10 (SEQ. ID NO:2) has been obtained the deprotection of the terminal amino of the resin (elimination of the Fmoc group) and the side chain of the Asu residuum (elimination of the allyl group) is carried out to obtain fragments 6 or 7 (SEQ. ID NO:5). Afterwards, and in the same way for both cases, the peptide-resin is treated with trifluoroacetic acid in the presence of carbocation captivators to deprotect and liberate the peptide from the resin. After purification, carbocalcitonin in its free state is obtained.

According, to another aspect and as mentioned above, the invention provides a procedure for obtaining said fragment 1 (SEQ. ID NO:1), as well for obtaining fragment 5 (SEQ. ID NO:3), the peptide-resin which is the precursor of fragment 3 (SEQ. ID NO:4), and for fragment 4 (SEQ. ID NO:3), the peptide-resin which is the precursor of fragment 2 (SEQ. ID NO:4) all of them used an Table 1 and 2 above for the preparation of carbocalcitonin according to the present invention.

Fragments 1 (SEQ. ID NO:1), 4 and 5 (SEQ. ID NO:3) are obtained starting with paramethylbenzhydrilamine resin (PMBHA) and incorporating an internal standard and a bridge group (handle) between the resin and the amino acids of the respective sequences.

To obtain fragment 1 (SEQ. ID NO:1), and because the terminal carboxy end of carbocalcitonin is a carboxyamide, the bridge group or handle which is incorporated is [1-(9H-fluoren-9-yl) methoxy-formamide]methyl -3,5-dimethoxyphenoxyvaleric acid (Fmoc-PAL) (Albericio et al. J.Org. Chem. (1990), 55, 3730) or alternatively p-[(R,S)-α-[1-(9H-fluoren-9-yl) methoxy-formamide]-2,4-dimethoxybenzyl]-phenoxy acetic acid (Fmoc-AM) (Atherton et al. J.Am. Chem. Soc. (1975), 97,6584. The incorporation of the bridge group is followed by linear synthesis, residuum by residuum, until the 22 amino acids are incorporated, using Fmoc as the protective group for the amino end in all cases. For the side chains Lys, Ser, Thr, Tyr Arg, Glu, His, Gln, Asn and Asp the protective groups are those indicated in the following Table 3:

TABLE 3

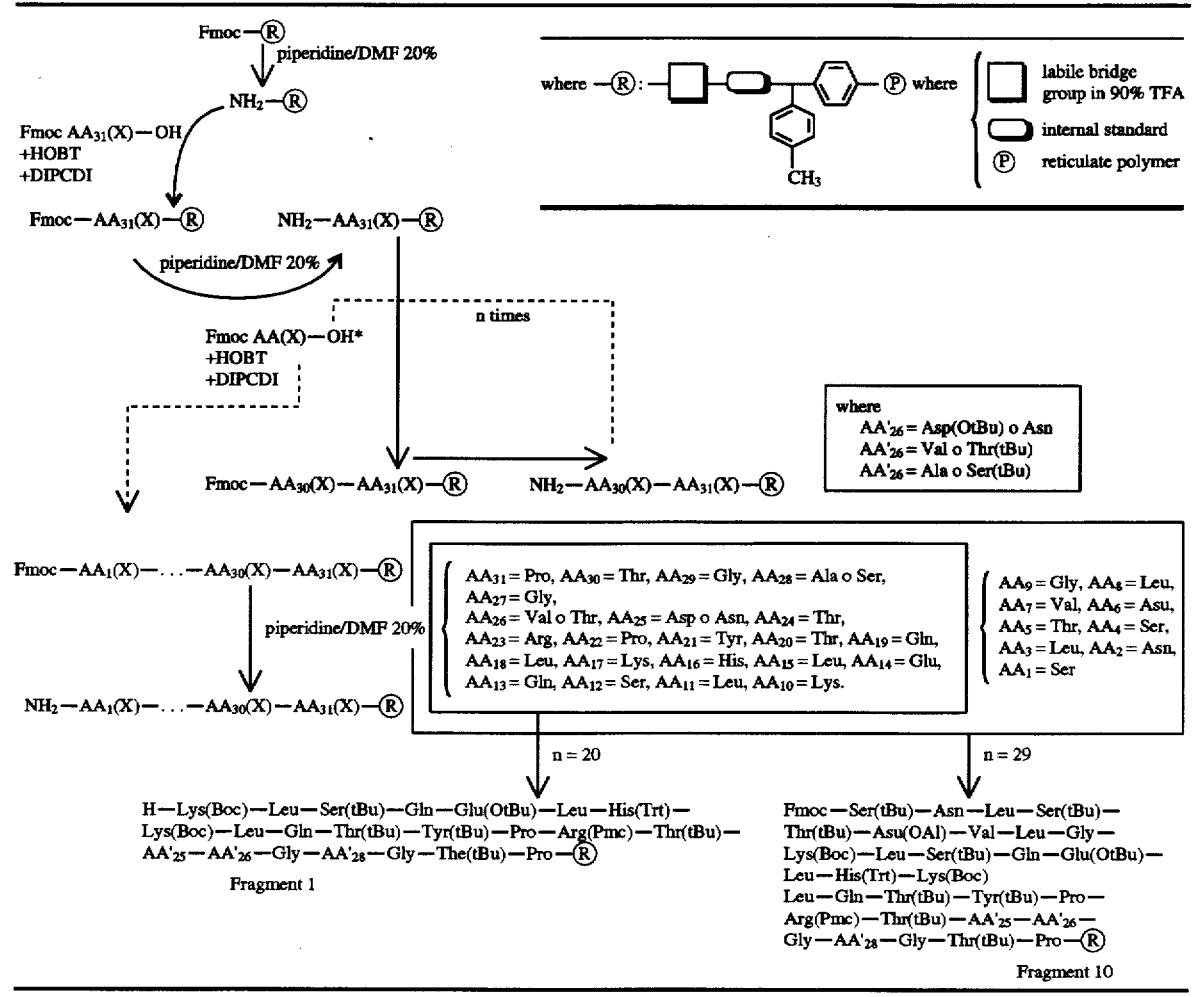

where R is defined as before.

To obtain fragment 4 (SEQ. ID NO:3), and because the terminal carboxy end must be carboxyacid, the resin [4-(hydroxymethyl)phenoxymethyl-copoly (styrene-1%divinylbenzene] (Wang resin) (Lit. S.:Wang.JACS 1973, 95,1328).

To obtain fragment 5 (SEQ. ID NO:3) and again because the terminal carboxy end must be carboxyacid, the bridge group or handle incorporated is 4(4-hydroxymethyl-3-methoxy-phenoxy)butyric acid (HMPB), also known as the Riniker Handle (Flörsheimer et al.). In both cases the incorporation of the bridge group is followed by linear synthesis, residuum by residuum, until the nine amino acids are incorporated, using the Fmoc group as the protective group for the amino end in all cases and the tBu group for the side chains Ser and Thr, as indicated in the following Table 4:

TABLE 4
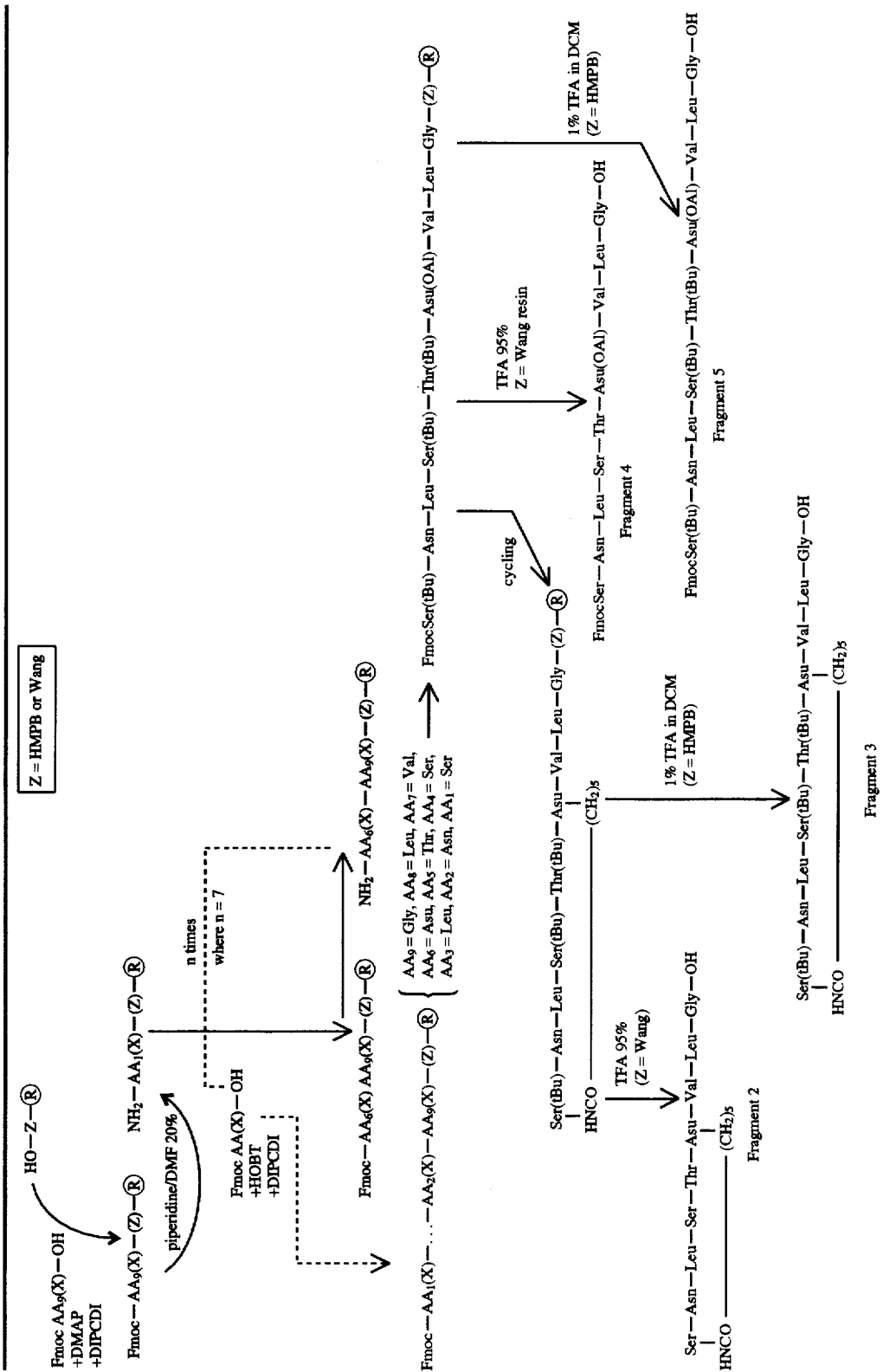

According to the previous table and to tables 1 and 2, the cyclization of the nonapeptide can be carried out before or after it has been incorporated with the fragement of 22 amino acids (fragment 1). To do this the side chain of the Asu residuum must be deprotected, this being done by means of Pd catalysis as has already been mentioned. Furthermore, the terminal amino end must also be deprotected, eliminating the Fmoc group with piperidine/DMF. The cycling is carried out by means of the standard method of forming amide bond, in particular with DIPCDI.

Referring once again to Table 4, the same steps as described above can also be carried out with the nonapeptide partially deprotected, i.e. without the tBu groups (fragments 2 (SEQ. ID NO:3) and 4(SEQ. ID NO:3)), working with Wang resin as shown in the diagram.

The abbreviations used in the present description have the following meanings:

AcOH: acetic acid
AcOEt: ethyl acid
Al: allyl
Ala: L-alanine
AM: p-[(R,S)-2,4-dimethoxy benzyl]-phenoxy acetic acid
Arg: L-arginine
Asn: L-asparagine
Asp: L-aspartic acid
Asu: L-α-aminosuberic acid
Boc: t-butoxycarbonyl
DCM: dichloromethane
DIEA: N,N'-diisopropyllethyl amine
DIPCDI: dilosopropylcarbodiimide
DMAP: dimethylaminopiridine
DMF: N,N'-dimethylformamide
EDT: 1,2-ethandithiol
Fmoc: 9-fluorenylmethoxycarbonyl
Fmoc OSu: 9-fluorenylmethoxycarbonyl N-hydroxysuccinimide ester
Gln: L-glutamine
Glu: L-glutamic acid
Gly: L-glycine
HBTU: 2-(1H-benzotriazole-1-yl)-1,1,3,3-tetramethyluronio hexafluorophosphate
His: L-histidine
HMPB: 4(4-hydroxymethyl-3-methoxyphenoxy)butyric acid
HOBT: N-hydroxybenzotriazole
HPLC: high pressure liquid chromatography
Ile: L-isoleucine
Leu: L-leucine
Lys: L-lysine
MeOH: methanol
PAL: aminomethyl-3,5-dimethoxyphenoxyvaleric acid
pMBHA: para-methylbenzhydrilamine
Pmc: 2,2,5,7,8-pentamethylchroman-6-sulphonyl
Pro: L-proline
PyBOP: benzotriazole-1-yl-oxy-tris-pirrodoline-phosphonide hexafluoraphosphate
Ser: L-serine
tBu: tert-butyl
TFA: trifluoroacetic acid
THF: tetrahydrofuran
Thr: L-treonine
TLC: thin film chromatography
Tos: tosyl
Trt: trityl
Tyr: L-tyrosine
Val: L-valine The invention is illustrated below by means of the following non-limiting examples, in which $AA_{25}$Asp or Asn, $AA_{26}$=Val or Thr, $AA_{28}$=Ala or Ser and $AA'_{25}$=Asp(OtBu) or Asn, $AA'_{26}$=Val or Thr(tBu), $AA'_{28}$=Ala or Ser(tBu).

EXAMPLE 1

Protection of side chain of aminosuberic acid (Asu). Obtaining w-allyl ester of L-α-aminosuberic acid (H-Asu (OAl)—OH).

1.134 g (6 mmol) of L-α-aminosuberic acid are suspended in 30 ml of allylalcohol (previously dried over a 3 Å sieve. In a nitrogen atmosphere, 1.9 ml (15 mmol) of chlorotrimethylsilane are added to the suspension drop by drop and the resulting solution is shaken for 20 hours at room temperature, the progress of the reaction being checked by means of TLC (AcOEt/AcOH 99/1). 200 ml of cold diethyl ether are added and the precipitate which appears is separated by centrifuging. It is then resuspended in ether and the same operation is repeated two more times. 915 g of a white solid are obtained, corresponding to the hydrochloride of the product. The mother water cools down (+4° C.) and the precipitate which appears is also centrifuged and washed with ether to obtain 135 mg more the product. The overall yield is 66%.

$^1$H RMN (CD$_3$OD, 200 MHz)δ: 5.93 (ddt, 1H, —C$\underline{H}$=CH$_2$), 5.4–5,15(m, 2H, —CH=C$\underline{H}_2$), 4.58 (d, 2H, J=5.5 Hz, COO—C$\underline{H}_2$), 3.97 (t, 1H, J=6 Hz, C$\underline{H}$—COOH), 2.33 (t, 2H, J=7.32 Hz, C$\underline{H}_2$—COO), 2.05–1.3 (m, 8H, CH—C$\underline{H}_2$—C$\underline{H}_2$—C$\underline{H}_2$—C$\underline{H}_2$).

EXAMPLE 2

Protection of α-amino group of aminosuberic acid. Obtaining Fmoc-Asu(OA)—OH.

1.05 g (.3.9 mmol) of Asu(OAl)-HCl are dissolved in 25 ml of an aqueous solution of 10% Na$_2$CO$_3$, ensuring that the pH does not exceed the value of 10. The resulting solution is cooled to 0° C. and a suspension 1.31 g (3.9 mmol) of Fmoc-OSu in 6.5 ml of acetone is added drop by drop. The suspension is shaken constantly and kept at the same temperature for 1 hour. When this time has elapsed it is left to reach room temperature and the reaction is checked with TLC (CHCl$_3$/MeOH/AcOH 90/8/2). After 3 hours the suspension will have disappeared and a transparent solution is observed. The solution is poured onto 200 ml of a mixture of ice and water and washed diethyl ether (4×30ml). The aqueous phase is cooled to 0° C. and acidified to pH=5.5 using dilute HCl solution, observing the precipitation of the Fmoc-ASu(OAl)—OH. The suspension is extracted with AcOEt (4×100 ml), reacidifying in each extraction in order to maintain a pH of 5.5. The collection of organic phases is dried on MgSO$_4$ and the solvent is eliminated under low pressure. An oil is thereby obtained which crystallizes to give the product in the form a white, friable solid (1.39 g/yield 79%).

$^1$H RMN (CDCl$_3$, 200 MHz) δ: 8.07 (width), 7.8–7.2 (m, 8H), 5.9 (ddt, -1H, —C$\underline{H}$=CH$_2$), 5.4 (d, 1H, J=9.7 HZ; C$\underline{H}$ (Fmoc)), 5.35–5.15 (m, 2H, —CH=C$\underline{H}_2$), 4.58 (d, 2H, $CH_2$—COO—$CH_2$), 4.43 (dd, 2H, $CH_2$ (Fmoc)), 4.21 (t, 1H, $CH$—COOH), 2.34 (t, 2H, J=7.6 Hz, $CH_2$—COO—), 2-1.2 (m, 8H, $CH_2$—$CH_2$—$CH_2$—$CH_2$—COO—).

EXAMPLE 3

Incorporation of an internal standard. Obtaining Boc-Ile-pMBHA.

1.658 g (6.9 mmoles) of BocIle are incorporated onto 4 g of p-methylbenzhydrilamine resin of 0.69 mmol/g resin as an internal standard by means of the synthesis programme described below:

| Step | Reagent | Repetitions | Time |
|---|---|---|---|
| 1 | TFA 40% | 1 | 2' |
| 2 | TFA 40% | 1 | 20' |
| 3 | DCM | 5 | 1' |
| 4 | DIEA 5% | 3 | 2' |
| 5 | DCM | 5 | 1' |
| 6 | Boc aa | — | + |
| 7 | HOBt | — | + |
| 8 | DIPCDI | — | 40' |
| 9 | DCM | 5 | 1' |
| 10 | check with ninhydrin, if + return to 6, if − continue | | |
| 11 | DCM | 5 | 1' |
| 12 | TFA 40% | 1 | 2' |
| 13 | TFA 40% | 1 | 20' |
| 14 | DCM | 5 | 1' |
| 15 | DIEA 5% | 3 | 2' |
| 16 | DCM | 5 | 1' |

EXAMPLE 4

Incorporation of Riniker handle. Obtaining 4(4-hydroxymethyl-3-methoxyphenoxy) butyramide-Ile-pMBHA.

There then follows the incorporation of 4(4-hydroxymethyl -3-methoxyphenoxy) butyric acid, also known as the Riniker handle (HMPB). This is carried out by reacting 4 g of the resin (fNH$_2$=0.69. mmol/g of resin), after it has been previously functionalized with the internal standard, with 1 g (4.14 mmoles of, 1.5 equivalents) of 4(4-hydroxymethyl -3-methoxyphenoxy) butyric acid, 0.62 g (4.14 mmoles, 1.5 equivalents) of HOBt and 641 μl (4.14 mmoles; 1.5 equivalents) using DMF as the solvent. The reaction time is 90'. After this time has elapsed, the resin is washed five times with DCM and the Kaiser is used to check that there are no free amines. If there are, the coupling process must be repeated.

EXAMPLE 5

Incorporation of the first amino acid. Obtaining Fmoc-Gly-Riniker handle-Ile-pMBHA.

The incorporation of the first amino acid, in this case glycine, implies the formation of an ester-type link between the handle and the Fmoc Gly derivative. For this kind of incorporation the resin is reacted with 4.1 g (5 equivalents) of Fmoc Gly in the presence of 168 mg (0.5 equivalents) of DMAP and 2.094 ml (5 equivalents) of DIPCDI in DMF for 90". Once the reaction is complete the resin is washed five times with DMF. An amino acid analysis or an acid hydrolysis of the resin gives the ratio of the Ile amino acid (internal standard) and the first amino acid Gly. In this way the real functionalization of the resin is known, normally varying between 0.35–0.69 mmol/g.

EXAMPLE 6

Incorporation of the first amino acid onto the Wang resin. Obtaining Fmoc-Gly-Wang resin.

This involves the same steps as example 5 except that the amino acid analysis is not carried out due to the absence of the internal standard.

EXAMPLE 7

Incorporation of the remaining amino acids. Obtaining FmocSer$^{(tBu)}$-Asn-Leu-Ser(tBu)-Thr(tBu)-Asu(OAl)-Val-Leu-Gly-handle Riniker-Ile-pMBHA or FmocSer(tBu)-Asn-Leu-Ser(tBu)-Thr (tBu)-Asu(OAl)-Val-Leu-Gly-Wang resin (SEQ. ID NO:4).

The incorporation of the remaining amino acids is carried out by following a synthesis programme such as the one described below:

| Step | Reagent | Repetitions | Time |
|---|---|---|---|
| 1 | DMF | 5 | 1' |
| 2 | pip/DMF 20% | 1 | 1' |
| 3 | pip/DMF 20% | 1 | 5' |
| 4 | DMF | 5 | 1' |
| 5 | Fmoc aa | — | + |
| 6 | HOBt | — | + |
| 7 | DIPCDI | — | 40' |
| 8 | DMF | 5 | 1' | check with ninhydrin, if + return to 5, if − continue with step 1 and the next amino acid.

In order to evaluate the synthetic purity of the totally deprotected 1–9 peptide, 20 mg of H-Ser(tBu)-Asn-Leu-Ser (tBu)-Thr(tBu)-Asu(OAl)-Val-Leu-Gly-Riniker handle-Ile-pMBHA (SEQ. ID NO:7) are treated with 900 μl of TFA, 50 μl of thioanisole, 30 μl of EDT and 20 μl of anisole for 2 hours at room temperature in a reactor provided with a filter plate (this treatment does not affect the allyl group, which remains unalterable). The filtrate is collected in a tube with cold, dry diethyl ether. The precipitation of the free peptide is observed and after centrifuging the floating material is decanted. The pellet is resuspended once again in cold, dry ether to eliminate the scavengers (EDT, thioanisole, anisole). This operation is repeated five times. Afterwards the pellet is dried and then dissolved in 1 ml of 10% acetic acid solution. 40 μl of the peptide solution are injected into HPLC with a gradient of 5–85% B, where A: H$_2$O 0.045% TFA and B: CH$_3$CN 0.035% TFA, in a Vydac column C18 5 μm, 25×0.46 cm. An amino acid analysis of a hydrolysis of the peptide-resin at 150° C. for 3 hours with a mixture of HCl/propanoic acid gives the following composition Asp 1.01 (1), Thr 0.8 (1)0 Ser 1.8 (2), Gly 1.2 (1), Ile 1.5–1 (1), Leu 1.99 (2), Val. 0.89 (1), Asu(OAl) 0.95 (1).

EXAMPLE 8

Deprotection of the α-amino of the terminal amino residuum (Ser) and of the side chain of the residuum Asu. Obtaining H-Ser(tBu)-Asn-Leu-Ser(tBu)-Thr(tBu)-Asu-Val-Leu-Gly-HMPB-Ile-pMBHA (SEQ. ID NO:3) or H-Ser (tBu)-Asn-Leu-Ser(tBu)-Thr-(tBu)-Asu-Val-Leu-Gly-Wang (SEQ. ID NO:3) resin Once the synthesis of the totally deprotected peptide is complete, there follows the process of deprotecting the -amino group of the terminal residuum (protected with Fmoc). This deprotection is carried out by treating the resin, washed in DHF, with a 20% solution of piperidine/DMF twice for 1 and 5 minutes. The resin is washed with DMF, DCM and is dried at low pressure.

Afterwards the side chain of the Asu residuum is deprotected. 200 mg of the peptide-resin are into a reactor provided with a filter plate in an atmosphere of helium. A separate solution is also prepared in an atmosphere of helium, said solution containing 7 mg of Pd(PPh$_2$)$_4$, 250 mg of PPh and 200 μl of morpholine, all dissolved in 3 ml of THF which has previously degassed by bubbling with helium. This solution is added to the peptide-resin and the mixture is kept under helium for 60 hours, shaking periodically. When this time has elapsed the peptide-resin is filtered and washed thoroughly with THF, DMF and DCM. Finally it is dried. In order to evaluate the degree of deprotection of the allyl group, 20 mg of the peptide-resin are treated with 950 μl of TFA, 30 μl of DCM and 20 μl of anisole for 2 hours at room temperature in a reactor provided with a filter plate. The filtrate is collected in a tube with cold, dry diethyl ether. The precipitation of the free peptide is observed and after centrifuging the floating material is decanted. The pellet is resuspended once again in cold, dry ether. This operation is repeated five times. Afterwards the pellet is dried and then dissolved in 1 ml of 10% acetic acid solution. 40 μl of the peptide solution are injected into HPLC with a gradient of 5–85%, B, where A: H$_2$O 0.045% TFA and: B: CH$_3$CN 0.035% TFA, in a Vydac column C$_{18}$ 5 μm, 25×0.46 cm. The deprotection varies around 90%.

EXAMPLE 9

Cycling of 1–9 peptide on resin. Obtaining

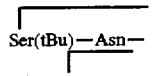

Leu—Ser(tBu)—Thr(tBu)—Asu—Val—Leu—Gly—HMPB—Ile—pMBHA (SEQ. ID NO: 4) or Ser(tBu)—

Asn—Leu—Ser(tBu)—Thr(tBu)—Asu—Val—Leu—Gly—Wang (SEQ. ID NO: 4) resin.

The fragment 1–9 is cycled with the terminal and acid amine groups of the side chain of the Asu residuum. This is also carried out in reactor with a filter plate. 60 mg of the peptide-resin, 16.2 μl of DIPCDI (6 equivalents) and 15.6 mg of HOBt (6 equivalents) are introduced dissolved in DMF. The reaction is checked using the Kaiser test and after 21 hours the resin is filtered and washed with DMF and DCM. In order to evaluate the purity of the peptide the same process as described for the deprotected peptide in example 8 is carried out.

EXAMPLE 10

Liberation of cyclic 1–9 fragment from resin. Obtaining

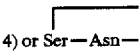

Ser(tBu)—Asn—Leu—Ser(tBu)—Thr(tBu)—Asu—Val—Leu—Gly—OH (SEQ. ID NO: 4) or Ser—Asn—

Leu—Ser—Thr—Asu—Val—Leu—Gly—OH (SEQ. ID NO: 4).

The peptide-resin H-Ser(tBu)-Asn-Leu-Ser(tBu)-Thr(tBu)-Asu-Val-Leu-Gly-Riniker handle-Ile-pMBHA is treated with a 1% solution of TFA in DCM 4 or 5 times over intervals of 15 minutes. Pyridine is added to the filtrates until it they are neutralized and the DCM is eliminated at low pressure. The white solid obtained is washed repeatedly with water and then dried.

Alternatively, the peptide-resin H-Ser(tBu)-Asn-Leu-Ser(tBu)-Thr(tBu)-Asu-Val-Leu-Gly-Wang resin (SEQ. ID NO:4) is treated with a solution containing TFA/DCM/anisole in the proportions 95/3/2 for 2 hours in a reactor provided with a filter plate. When this time has elapsed the acidic solution is poured onto cold, dry ether and the solid which appears is separated by centrifuging. This solid is washed with ether two more times and then dried.

EXAMPLE 11

Liberation of the totally or partially protected nonapeptide from the resin. Obtaining FmocSer(tBu)-Asn-Leu-Ser(tBu)-Thr(tBu)-Asu(OAl)-Val-Leu-Gly—OH or FmocSer-Asn-Leu-Ser-Thr-Asu-(OAl)-Val-Leu-Gly—OH (SEQ. ID NO:3).

The same procedure as the previous example is carried out for both resins.

EXAMPLE 12

Incorporation of the Fmoc AM handle onto Boc-Ile-pMBHa. Obtaining p-[(R,S)-a-[1-(9H-fluoren-9-Il)metoxi-formamido]-2,4-dimetoxyl benzyll]-fenoxiacetamido-Ile-pMBHA There then follows the incorporation of p-[(R,S)-a-[1-(9H-fluoren-9-yl) methoxy-formamide]-2,4-dimethoxy benzyl]-phenoxy acetic acid (Fmoc-AM). This is carried out by reacting 4 g of the resin (0.69 mmoles/g of resin), after it has been previously functionalized with the internal standard (following the protocol described in example 1), with 2.23 g (4.14 mmoles, 1.5 equivalents) of p-[(R,S)-a-[1-(9H-fluoren-9-yl) methoxy-formamide]-2,4-dimethoxy benzyl]-phenoxy acetic acid, 0.62 g (4.14 mmoles, 1.5 equivalents) of HOBt and 641 μl (4.14 mmoles, 1.5 equivalents) using DHF as the solvent. The reaction time is 90'. After this time has elapsed, the resin is washed five times with DCM and the Kaiser test is used to check that there are no free amines. If there are, the coupling process must be repeated.

EXAMPLE 13

Incorporation of the Fmoc-PAL handle onto Boc-Ile-pMBHa. Obtaining [1-(9H-fluoren-9-Il)metoxi-formamido] metll-3,5-dimetoxlvaleriamido-Ile-pMBHA There then follows the incorporation of [1-(9H-fluoren-9-yl) methoxy-formamide] methyl-3,5-dimethoxyvaletic acid (Fmoc-PAL); This is carried out by reacting 4 g of the resin (0.69 mmol/g of resin), after it has been previously functionalized with the internal standard (following the protocol described in example 1), with 1.89 g (4.14 mmol, 1.5 equivalents) of [1-(9H-fluoren-9-yl) methoxy-formamide] methyl-3,5-dimethoxyvaleric acid, 0.62 g (4.14 mmol, 1.5 equivalents) of HOBt and 641 μl (4.14mmol, 1.5 equivalents) using DMF as the solvent. The reaction time is 90'. After this time has elapsed, the resin is washed five times with DCM and the Kaiser is used to check that there are no free amines. If there are, the coupling process must be repeated.

EXAMPLE 14

Incorporation of the remaining amino acids. Obtaining Fmoc Lys(Boc)-Leu-Ser(tBu)-Gln-Glu(OtBu)-Leu-His-

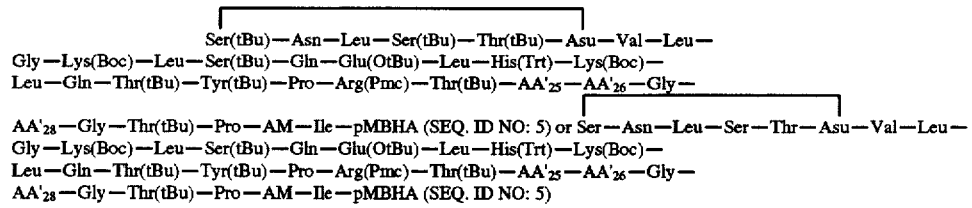

(Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr(tBu)-Pro-AM-Ile-pMBHA (SEQ. ID NO:1).

The incorporation or the remaining amino acids is carried out by following a synthesis programme such as the one described below:

| Step | Reagent | Repetitions | Time |
|---|---|---|---|
| 1 | DMF | 5 | 1' |
| 2 | pip/DMF 20% | 1 | 1' |
| 3 | pip/DMF 20% | 1 | 5' |
| 4 | DMF | 5 | 1' |
| 5 | Fmoc aa | — | + |
| 6 | HOBt | — | + |
| 7 | DIPCDI | — | 40' |
| 8 | DMF | 5 | 1' | check with ninhydrin, if + return to 5, if − continue with step 1 and the next amino acid.

In order to evaluate the synthetic purity of the totally deprotected 10–31 peptide, 20 mg of Fmoc Lys(Boc)-Leu-Ser(tBu)-Gln-Glu(OtBu)-Leu-His(Trt)-Lys (Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr (tBu)-Pro-AM-Ile-pMBHA (SEQ. ID NO:8) are treated with 900 µl of TFA, 50 µl of thioanisole, 30 µl of EDT and 20 µl of anisole for 2 hours at room temperature in a reactor provided with a filter plate. The filtrate is collected in a tube with cold, dry diethyl ether. The precipitation of the free peptide is observed and after centrifuging the floating material is decanted. The pellet is resuspended once again in cold, dry ether to eliminate the scavangers (EDT, thloanisole, anisole). This operation is repeated five times. Afterwards the pellet is dried and then dissolved in 1 ml of a solution of 10% acetic acid. 40 µl of the peptide solution are injected into HPLC with a gradient of 5–85% B, where A: H$_2$O 0.045% TFA and B: CH$_3$CN 0.035 % TFA, Vydac C 5 µm, 25×0.46 cm. An amino acid analysis of a hydrolysis of the peptide-resin at 150° C. for 3 hours with a mixture of HCl/propanoic acid gives the following composition Asp 1.06 (1), Thr 2.8 or 4.0 (3 or 4), Ser 0.96 or 2.0 (1 or 2), Glu 3.01 (3), Gly 2.2 (2), Pro 1.98 (2), Ile 0.9 (1), Leu 3.0 (3), Tyr 0.8 (1), His 0.92 (1), Lys 1.8 (2), Arg 1.03 (1), Ala 1.1 or 0 (1 or 0), Val 0.97 or 0 (1 or 0).

EXAMPLE 15

Incorporation of the protected or deprotected and cycled nonapeptide onto the peptide-resin of the protected 10–31 fragment 1. Obtaining 2.03 g of the peptide-resin 10–31 are treated with piperidine/DMF for 3 minutes. The operation is repeated two more times and the resin is then washed 5 times for 1 minute with DMF. 315 mg (2.5 equivalents) of HBTU (or alternatively the mmoles equivalents of PyBOP, 431 mg) and 124 mg (2.5 equivalents) of HOBT dissolved in DMF are added to the resin, forming the most homogeneous mass possible with the resin. 2.5 equivalents of totally protected 1–9 cyclic peptide 1–9 (922 mg) or totally deprotected cyclic peptide 1–9 (741 mg) are dissolved in the minimum quantity possible of DMF and added to the resin. Finally 296 µl (5 equivalents) of DIEA are added. The resin is shaken well until it is homogeneous. The reaction acquires an orange colour. One hour and 30 minutes later the Kaiser test on one aliquot part of the resin gives a negative result and the incorporation reaction can be considered complete. The resin is filtered and washed repeatedly with DMF.

EXAMPLE 16

Linear synthesis of fragment 10. Obtaining FmocSer-(tBu)-Asn-Leu-Ser(tBu)-Thr(tBu)-Asu(OAl)-Val-Leu-Gly-Lys (Boc)-Leu-Ser(tBu)-Gln-Glu(OtBu)-Leu-His(Trt-Lys (Boc)-Leu-Gln-Thr(tBu)-Tyr(tBu)-Pro-Arg(Pmc)-Thr(tBu)-AA'$_{25}$-AA'$_{26}$-Gly-AA'$_{26}$-Gly-Thr(tBu)-Pro-AM-Ile-pMBHA (SEQ. ID NO:2)

There then follows the incorporation of all of the amino acids onto the peptide-resin obtained as explained in examples 12 and 13, i.e. onto AM-Ile-pMBHA or PAL-Ile-pMBHA. This incorporation is carried out in the same way as indicated in example 14, as is the evaluation of the synthetic purity of the final product. An amino acid analysis of a hydrolysis of the peptide-resin at 150° C. for 3 hours with a mixture of HCl/propanoic acid gives the following composition Asp 2.08 (2), Thr 3.76 or 4.2 (4 or 5), Ser 2.84 or 3.62 (3 or 4), Glu 3.01 (3), Gly 3.3 (3), Pro 1.98 (2), Ile 0.9 (1), Leu 4.95 (5), Tyr 0.8 (1), His 0.92 (1), Lys 1.8 (2), Arg 1.03 (1), Ala 1.1 or 0 (1 or 0), Val 1.95 or 0.9 (2 or 1), Asu(OAl) 0.96 (1).

EXAMPLE 17

Incorporation of the protected or deprotected nonapeptide without cycling onto the peptide-resin of the protected 10–31 fragment 1. Obtaining: FmocSer(tBu)-Asn-Leu-Ser(tBu)-Thr(tBu)-Asu(OAl)-Val-Leu-Gly-Lys(Boc)-Leu-Ser(tBu)-Gln-Glu(OtBu)-Leu-His(Trt)-Lys(Boc)-Leu-Gln-Thr(tBu)-Tyr(tBu)-Pro-Art (Pmc)-Thr(tBu)-AA'$_{25}$-AA'$_{26}$-Gly-AA'$_{289}$-Gly-Thr(tBu)-Pro-AM-Ile-pMBHA or FmocSer-Asn-Leu-Ser-Thr-Asu-(OAl)Val-Leu-Gly-Lys(Boc)-Leu-Ser (tBu)-Gln-Glu(OtBu)-Leu-His(Trt)-Lys(Boc)-Leu-Gln-Thr(tBu)-Tyr(tBu)-Pro-Art(Pmc)-Thr(tBu)-AA'$_{25}$-AA'$_{26}$-Gly-AA'$_{26}$-Gly-Thr (tBu)-Pro-Am-Ile-pMBHA (SEQ. ID NO:2)

Follow the same method as described in the previous example.

EXAMPLE 18

Deprotection of the terminal O-amino and the side chain of the residuum Asu followed by cycling of the peptide 1–31. Obtaining:

┌─────────────────────────────────────────────────┐
Ser(tBu)—Asn—Leu—Ser(tBu)—Thr(tBu)—Asu—Val—Leu—Gly—Lys(Boc)—
Leu—Ser(tBu)—Gln—Glu(OtBu)—Leu—His(Trt)—Lys(Boc)—Leu—Gln—
Thr(tBu)—Tyr(tBu)—Pro—Arg(Pmc)—Thr(tBu)—AA'$_{25}$—AA'$_{26}$—Gly—AA'$_{28}$—Gly—
Thr(tBu)—Pro—AM—Ile—pMBHA (SEQ. ID NO: 5) or

┌─────────────
                                            Ser—Asn—Leu—Ser—
─────┐
Thr—Asu—Val—Leu—Gly—Lys(Boc)—Leu—Ser(tBu)—Gln—Glu(OtBu)—Leu—
His(Trt)—Lys(Boc)—Leu—Gln—Thr(tBu)—Tyr(tBu)—Pro—Arg(Pmc)—
Thr(tBu)—AA'$_{25}$—AA'$_{26}$—Gly—AA'$_{28}$—Gly—Thr(tBu)—Pro—AM—Ile—pMBHA (SEQ. ID NO: 5)

The same procedure as described in example 8 is carried out for the deprotection and that described in example 9 for cycling.

EXAMPLE 19

Breaking the resin and deprotection of the peptide 1–31 in any of its forms. Obtaining:

┌─────────────
                                            Ser—Asn—Leu—Ser—
─────┐
Thr—Asu—Val—Leu—Gly—Lys—Leu—Ser—Gln—Glu—Leu—His—Lys—Leu—Gln—Thr—Tyr—Pro—
Arg—Thr—AA$_{25}$—AA$_{26}$—Gly—AA$_{28}$—Gly—Thr—Pro—NH$_2$ (SEQ. ID NO: 6)

The dry peptide-resin 1–31 is treated with TFA/DCM/anisole (95:3:2) for 2 hours at room temperature. It is then poured onto 100 ml of cold, dry diethyl ether. The white precipitate which is obtained is separated by centrifuging. The solid is resuspended once again in diethyl ether and centrifuged again. This operation is repeated five more times. Finally, the solid obtained is dried and then, dissolved in 10% AcOH, is purified with an HPLC preparation with a gradient of 5–65% B, where Al H$_2$O 0.05% TFA and B: CH$_3$CN 0.035% TFA. Vydac C18 15–20 µm. 25×1 cm.

We claim:

1. A procedure for obtaining carbocalcitonin and its pharmaceutically acceptable acid addition salts or complexes thereof, by means of solid phase synthesis on polymeric supports and with the intervention of Fmoc/tBu characterized in that it comprises the stages of:

(a) condensing fragment 1 (SEQ. ID NO.: 1) consisting of the docosapeptide corresponding to the carboxamide end of the carbocalcitonin sequence, protected and anchored on resin, Fragment 1 having the sequence:

Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{26}$-Gly-Thr-Pro-®
(SEQ. ID NO: 1)

wherein -® has the following formula with bridge group, internal structure and reticulate polymer:

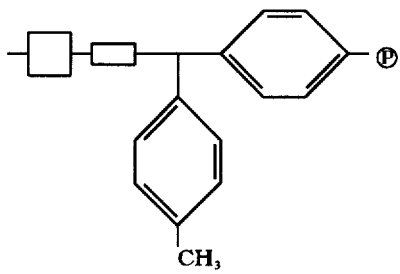

where ☐ is a bridge group,

☐ is an internal standard, and Ⓟ is a reticulate polymer, with fragment 2, consisting of the nonapeptide corresponding to the amino end of the carbocalcitonin sequence, with the cycle formed and with the absence of the protective groups for the side chains Ser and Thr, Fragment 2 having the sequence:

Ser—Asn—Leu—Ser—Thr—Asu—Val—Leu—Gly—OH
(SEQ. ID NO: 4)

or, alternatively, with fragment 3, also consisting of the nonapeptide corresponding to the amino end, with the cycle formed, but with the side chains of the residue Ser and Thr protected with the group tBu, Fragment 3 having the sequence:

Ser(tBu)—Asn—Leu—Ser(tBu)—Thr(tBu)—Asu—

Val—Leu—Gly—OH (SEQ. ID NO.: 4)

b) subjecting the peptide-resin resulting from the condensation and cycle formation reactions, that is, fragments 6 or 7 (SEQ. ID NO.: 5) wherein AA'$_{25}$ is selected from the group consisting of Asp and Asn, AA'$_{26}$ is selected from the group consisting of Val and Thr, and AA'$_{28}$ is selected from the group consisting of Ala and Ser, fragments 6 (X=H) and 7 (X=tBu) having the sequence:

Ser(X)—Asn—Leu—Ser(X)—Thr(X)—Asu—Val—Leu—Gly—

Lys(Boc)—Leu—Ser(tBu)—Gln—Glu(OtBu)—Leu—His(Trt)—

Lys(Boc)—Leu—Gln—Thr(tBu)—Tyr(tBu)—Pro—Arg(Pmc)—

-continued
Thr(tBu)—AA'$_{25}$—AA'$_{26}$—Gly—AA'$_{28}$—Gly—Thr—Pro—Ⓡ
(SEQ. ID NO: 5)

to an acidic treatment of deprotection of the side chains and deanchoring of the resin to obtain the carbocalcitonin peptide.

2. A procedure according to claim 1 characterized in that fragments 2 and 3 (SEQ. ID NO.: 4) are obtained from para-methylbenzhydrilamine resin by incorporating the internal standard and the bridge group between the resin and the sequence of amino acids, this being followed by linear synthesis, residuum by residuum, until the 9 amino acids of fragments 2 or 3 have been incorporated.

3. A procedure according to claim 2, wherein the linear synthesis of the fragment of 9 amino acids, the group Fmoc is used for the amino end in all cases, and for the side chains Lys, Ser, Thr, Cys and Asn the protective groups indicated for said chains in the formula of fragments 2, 3 (SEQ. ID NO.: 4), 4 (SEQ. ID NO.: 3) and 5 (SEQ. ID NO.: 4) are used.

4. A procedure for obtaining carbocalcitonin and its pharmaceutically acceptable acid addition salts or complexes thereof, by means of solid phase synthesis on polymeric supports and with the intervention of Fmoc/tBu comprising the steps of:

(a) condensing fragment 1 (SEQ. ID NO.: 1) consisting of the docosapeptide corresponding to the carboxamide end of the carbocalcitonin sequence, protected and anchored on resin; fragment 1 having the sequence:

Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg (Pmc)-Thr(tBu)-AA'$_{25}$-AA'$_{26}$-Gly-AA'$_{28}$-Gly-Thr-Pro-®
(SEQ. ID NO.: 1)

wherein -® has the following formula with bridge group, internal structure and reticulate polymer:

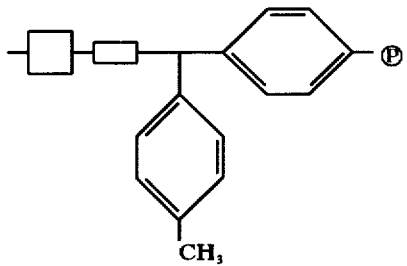

where ☐ is a bridge group,

☐ is an internal standard, and Ⓟ is a reticulate polymer, with fragment 5 having the sequence:
FmocSer(tBu)-Asn-Leu-Ser(tBu)-Thr(tBu)-Asu(OAl)-Val-Leu-Gly—OH (SEQ. ID NO.: 3)

to obtain the peptide-resin corresponding to fragment 10 having the sequence:

FmocSer(tBu)-Asn-Leu-Ser(tBu)-Thr(tBu)-Asu(OAl)-Val-Leu-Gly-Lys(Boc)-Leu-Ser(tBu)-Gln-Glu(OtBu)-Leu-His (Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr-Pro-® (SEQ. ID NO.: 2)

which is subjected to a reaction of deprotection and cyclization to obtain fragment 7 (SEQ. ID NO.: 5) which is in turn subjected to the treatment of de-anchoring from the resin and then purified to obtain carbocalcitonin wherein AA'$_{25}$ is selected from the group consisting of Asp and Asn, AA'$_{26}$ is selected from the group consisting of Val and Thr, and AA'$_{28}$ is selected from the group consisting of Ala and Ser.

5. A procedure according to claims 1 or 4, characterized in that fragment 1 (SEQ. ID NO.: 1) is obtained from para-methylbenzhydrilamine resin by incorporating the internal standard selected from Ile or Ala and the bridge group selected from p[(R,S)-2,4-dimethoxybenzyl) phenoxy acetic acid or aminomethyl-3,5-dimethoxyphenoxyvaleric acid between the resin and the sequence of amino acids, this being followed by linear synthesis, residuum by residuum, until the 22 amino acids have been incorporated.

6. A procedure according to claim 5 characterized in that during the linear synthesis of the fragment of 22 amino acids the group Fmoc is used for the amino end in all cases and for the side chains Lys, Ser, Thr, Tyr, Arg, Glu, His, and Asp the protective groups indicated for said chains of the formula for fragment 1 (SEQ. ID NO.: 1) are used.

7. A procedure according to claims 1, or 4 characterized in that fragments 2, 3 (SEQ. ID NO.: 4), and 5 (SEQ. ID NO.: 3) are obtained from para-methylbenzhydrilamine resin by incorporating the internal standard and the bridge group between the resin and the sequence of amino acids, this being followed by linear synthesis, residuum by residuum, until the 9 amino acids have been incorporated.

8. A procedure according to claim 7, characterized in that in the linear synthesis of the fragment of 9 amino acids, the group Fmoc is used for the amino end in all cases, and for the side chains Lys, Ser, Thr, Cys and Asn the protective groups indicated for said chains in the formula of fragments 2, 3 (SEQ. ID NO.: 4) and 5 (SEQ. ID NO.: 4) are used.

9. A procedure for obtaining carbocalcitonin and its pharmaceutically acceptable acid addition salts or complexes thereof, by means of solid phase synthesis on polymeric supports and with the intervention of Fmoc/tBu comprising the steps of:

(a) condensing fragment 1 (SEQ. ID NO.: 1) consisting of the docosapeptide corresponding to the carboxamide end of the carbocalcitonin sequence, protected and anchored on resin; fragment 1 having the sequence:

Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr-Pro-Ⓟ (SEQ. ID NO.: 1)

wherein -Ⓟ ha the following formula with bridge group, internal structure and reticulate polymer:

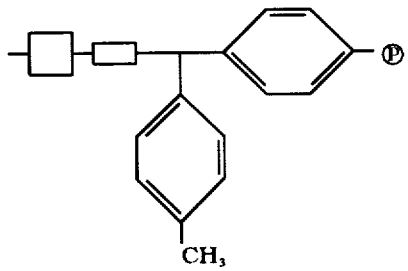

-continued where { ▢ is a bridge group,
▢ is an internal standard,
and { Ⓟ is a reticulate polymer, with fragment 4 having the sequence:

FmocSer-Asn-Leu-Ser-(tBu)-Thr-(tBu)-Asu(OAl)-Val-Leu-Gly—OH (SEQ. ID NO.: 3)

to obtain the peptide-resin which is fragment 9 having the sequence:

FmocSer-Asn-Leu-Ser(tBu)-Thr(tBu)-Asu-(OAl)-Val-Leu-Gly-Lys(Box)-Leu-Ser(tBu)-Gln-Glu(OtBu)-Leu-His(Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr-Pro-Ⓟ (SEQ. ID NO.:2)

which is subjected to the reaction steps of deprotection, cyclization, and de-anchoring from the resin and then purified to obtain carbocalcitonin wherein AA'$_{25}$ is selected from the group consisting of Asp and Asn, AA'$_{26}$ is selected from the group consisting of Val and Thr, and AA'$_{28}$ is selected from the group consisting of Ala and Ser, the side chains Lys, Ser, Thr, Tyr, Arg, Glu, His, Gln and Asp the protective groups are as indicated for said chains in the formula of fragment 1 (SEQ. ID NO.: 1).

10. A procedure according to claim 9 characterized in that fragment 1 (SEQ. ID NO.: 1) is obtained from para-methylbenzhydrilamine resin by incorporating the internal standard selected from Ile or Ala and the bridge group selected from p[(R,S)-2,4-dimethoxybenzyl)phenoxy acetic acid or aminomethyl-3,5-dimethoxypherioxyvaleric acid between the resin and the sequence of amino acids, this being followed by linear synthesis, residuum by residuum, until the 22 amino acids have been incorporated.

11. A procedure according to claim 10 characterized in that during the linear synthesis of the fragment of 22 amino acids the group Fmoc is used for the amino end in all cases, and for the side chains Lys, Ser, Thr, Tyr, Arg, Glu, His, Gln, and Asp the protective groups are as indicated for said chains in the formula of fragment 1 (SEQ. ID NO.: 1).

12. A method for forming carbocalcitonins in which a cyclic structure is formed between the side chain carboxylic acid of Asu and an amino functionality of a different amino acid comprising the steps of:

(a) incorporating Fmoc-Asu(ω-allyl)—OH into a polypeptide;

(b) incorporating at least one additional amino acid into the polypeptide of step (a);

(c) removing the ω-allyl group from the carboxylic acid side chain of Asu; and (d) cyclizing the polypeptide wherein the cyclic structure is formed between the side chain carboxylic acid of Asu and an amino functionality of a different amino acid, to form carbocalcitonin.

13. The method of claim 12 wherein the carbocalcitonins are selected from the group consisting of salmon, eel, human, porcine and bovine carbocalcitonins.

14. The method of claim 12 further comprising the steps of forming fragments 1 (SEQ. ID NO.: 1), 2 (SEQ. ID NO.: 4) and 3 (SEQ. ID NO.: 4) and then coupling fragment 1 (SEQ. ID NO.: 1) with one of fragments 2 (SEQ. ID NO.: 4) or 3 (SEQ. ID NO.: 4) to form one of fragments 6 (SEQ. ID NO.: 5) or 7 (SEQ. ID NO.: 5) wherein AA'$_{25}$ is selected from the group consisting of Asp and Asn, AA'$_{26}$ is selected from the group consisting of Val and Thr, and AA'$_{28}$ is selected from the group consisting of Ala and Ser, fragment 6(X=H) and 7(X=tBu) having the sequence:

Ser(X)—Asn—Leu—Ser(X)—Thr(X)—Asu—Val—Leu—Gly—Lys(Boc)—Leu—Ser(tBu)—Gln—Glu(OtBu)—Leu—His(Trt)—Lys(Boc)—Leu—Gln—Thr(tBu)—Tyr(tBu)—Pro—Arg(Pmc)—Thr(tBu)—AA'$_{25}$—AA'$_{26}$—Gly—AA'$_{28}$—Gly—Thr—Pro— ⓟ (SEQ. ID NO.: 5)

wherein -ⓟ has the following formula with bridge group, internal structure and reticulate polymer:

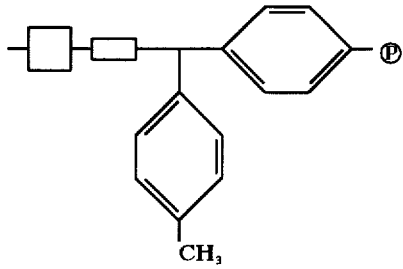

where { ☐ is a bridge group,
☐ is an internal standard, .

and ⓟ is a reticulate polymer,

15. The method of claim 12 further comprising the steps of forming fragments 1 (SEQ. ID NO.: 1) and 4 (SEQ. ID NO.: 4) and then coupling fragment 1 (SEQ. ID NO.: 1) with fragment 4 (SEQ. ID NO.: 4) to form fragment 9 (SEQ. ID NO.: 2) wherein AA'$_{25}$ is selected from the group consisting of Asp and Asn, AA'$_{26}$ is selected from the group consisting of Val and Thr, and AA'$_{28}$ is selected from the group consisting of Ala and Ser, fragment 9 having the sequence:

FmocSer-Asn-Leu-Ser-Thr-Asu-(OAl)-Val-Leu-Gly-Lys (Boc)-Leu-Ser(tBu)-Gln-Glu(OtBu)-Leu-His (Trt)-Lys (Boc)-Leu-Gln-Thr(tBu)-Tyr(tBu)-Pro-Arg(Pmc)-Thr (tBu)-AA'$_{25}$-AA'$_{26}$Gly-AA'$_{28}$-Gly-Thr-Pro-ⓟ(SEQ. ID NO. :2)

wherein -ⓟ has the following formula with bridge group, internal structure and reticulate polymer:

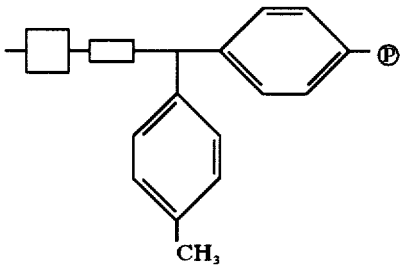

where { ☐ is a bridge group,
☐ is an internal standard, .

and ⓟ is a reticulate polymer,

16. The method of claim 12 further comprising the steps of forming fragments 1 (SEQ. ID NO.: 1) and 5 (SEQ. ID NO.: 3) and then coupling fragment 1 (SEQ. ID NO.: 1) with fragment 5 (SEQ. ID NO.: 3) to form fragment 10 (SEQ. ID NO.: 2) wherein in fragment 10 AA'$_{25}$ is selected from the group consisting of Asp and Asn, AA'$_{26}$ is selected from the group consisting of Val and Thr, and AA'$_{28}$ is selected from the group consisting of Ala and Ser, fragment 10 having the sequence:

FmocSer(tBu)-Asn-Leu-Ser(tBu)-Thr(tBu)-Asu(OAl)-Val-Leu-Gly-Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg (Pmc)-Thr(tBu)-AA'$_{25}$-AA'$_{26}$-Gly-AA'$_{28}$-Gly-Thr-Pro-ⓟ(SEQ. ID NO.: 2)

wherein -200 has the following formula with bridge group, internal structure and reticulate polymer:

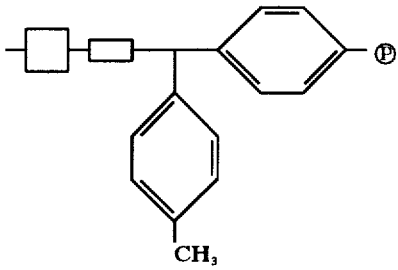

where { ☐ is a bridge group,
☐ is an internal standard, .

and ⓟ is a reticulate polymer,

17. A method for the solid-phase synthesis of carbocalcitonin comprising the steps of:
  selecting an insoluble solid support;
  chemically protecting the alpha-amino group of the carboxyl-terminal amino acid with Fmoc;
  coupling said carboxyl-terminal amino acid to said solid support;
  deprotecting said carboxyl-terminal amino acid;
  selecting and introducing additional Fmoc-protected amino acids;
  selecting Fmoc-Asu(ω-allyl)—OH as a protected Asu amino acid; and
  alternating the deblocking and coupling reaction to form carbocalcitonin.

18. A new peptide fragment for use in the synthesis of carbocalcitonin having the following sequence and structure, protected and anchored on resin:

Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg (Pmc)-Thr(tBu)-Asp(OtBu)-Val-Gly-Ala-Gly-Thr-Pro-ⓟ (SEQ. ID NO.: 1)

wherein -ⓟ has the following formula with bridge group, internal structure and reticulate polymer:

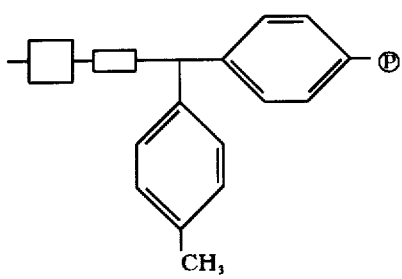

where
- ☐ is a bridge group,
- ☐ is an internal standard, and Ⓟ is a reticulate polymer, 19. A new peptide fragment for use in the synthesis of salmon or eel carbocalcitonin having the following sequence and structure:

```
┌─────────────────────┐
Ser—Asn—Leu—Ser—Thr—Asu—
                        Val—Leu—Gly—OH (SEQ. ID NO.: 4)
```

20. A new peptide fragment for use in the synthesis of salmon or eel carbocalcitonin having the following sequence and protected structure:

```
┌──────────────────────────────────┐
Ser(tBu)—Asn—Leu—Ser(tBu)—Thr(tBu)—Asu—Val—Leu—Gly—OH (SEQ. ID NO.: 4)
```

21. A new peptide fragment for use in the synthesis of salmon or eel carbocalcitonin having the following sequence and structure, protected and anchored on resin, wherein $AA'_{25}$ is selected from the group consisting of Asp and Asn, $AA'_{26}$ is selected from the groups consisting of Val and Thr, and $AA'_{28}$ is selected from the group consisting of Ala and Ser:

```
┌─────────────────────┐
Ser(X)—Asn—Leu—Ser(X)—Thr(X)—Asu—Val—Leu—Gly—Lys(Boc)—Leu—Ser(tBu)—Gln—Glu(OtBu)—Leu—
His(Trt)—Lys(Boc)—Leu—Gln—Thr(tBu)—Tyr(tBu)—Pro—Arg(Pmc)—Thr(tBu)—AA'25—AA'26—Gly—
AA'28—Gly—Thr—Pro— Ⓟ (SEQ. ID NO.: 5)
``` wherein X is H and -Ⓟ has the following formula with bridge group, internal structure and reticulate polymer:

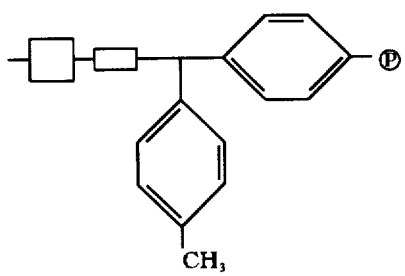

where
- ☐ is a bridge group,
- ☐ is an internal standard, and Ⓟ is a reticulate polymer, 22. A new peptide fragment for use in the synthesis of salmon or eel carbocalcitonin having the following sequence and structure, protected and anchored on resin, wherein $AA'_{25}$ is selected from the group consisting of Asp and Asn, $AA'_{26}$ is selected from the group consisting of Val and Thr, and $AA'_{28}$ is selected from the group consisting of Ala and Ser:

Ser(tBu)—Asn—Leu—Ser(X)—Thr(X)—Asu—Val—Leu—Gly—Lys(Box)—Leu—Ser(tBu)—Gln—Glu(OtBu)—Leu—His(Trt)—Lys(Boc)—Leu—Gln—Thr(tBu)—Tyr(tBu)—Pro—Arg(Pmc)—Thr(tBu)—AA'$_{25}$—AA'$_{26}$—Gly—AA'$_{28}$—Gly—Thr—Pro— ⓟ (SEQ. ID NO.: 5)

wherein -ⓟ has the following formula with bridge group, internal structure and reticulate polymer:

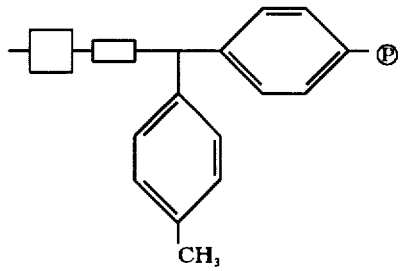

where ☐ is a bridge group,

▭ is an internal standard, and ⓟ is a reticulate polymer,

23. A new peptide fragment for use in the synthesis of salmon or eel carbocalcitonin having the following partially protected sequence and structure:

FmocSer-Asn-Leu-Ser-(tBu)-Thr-(tBu)-Asu(OAl)-Val-Leu-Gly—OH (SEQ. ID NO.: 3).

24. A new peptide fragment for use in the synthesis of salmon or eel carbocalcitonin having the following sequence and structure, protected and anchored in resin, wherein AA'$_{25}$ is selected from the group consisting of Asp and Asn, AA'$_{26}$ is selected from the group consisting of Val and Thr, and AA'$_{28}$ is selected from the group consisting of Ala and Ser having:

FmocSer-Asn-Leu-Ser-Thr-Asu(OAl)-Val-Leu-Gly-Lys(Boc)-Leu-Ser(tBu)-Gln-Glu(OtBu)-Leu-His(Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr-Pro-ⓟ(SEQ. ID NO.: 2)

wherein -ⓟ has the following formula with bridge group, internal structure and reticulate polymer:

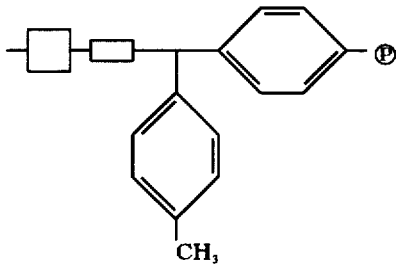

where ☐ is a bridge group,

▭ is an internal standard, and ⓟ is a reticulate polymer,

25. A new peptide fragment for use in the synthesis of salmon or eel carbocalcitonin having the following protected sequence and structure:

FmocSer(tBu)-Asn-Leu-Ser(tBu)-Thr(tBu)-Asu(OAl)-Val-Leu-Gly—OH (SEQ. ID NO.: 3).

26. A new peptide fragment for use in the synthesis of salmon or eel carbocalcitonin having the following sequence and structure, protected and anchored on resin, wherein AA'$_{25}$ is selected from the group consisting of Asp and Asn, AA'$_{26}$ is selected from the group consisting of Val and Thr, and AA'$_{28}$ is selected from the group consisting of Ala and Ser:

FmocSer(tBu)-Asn-Leu-Ser(tBu)-Thr(tBu)-Asu(OAl)-Val-Leu-Gly-Lys(Boc)-Leu-Ser(tBu)-Gln-Glu(OtBu)-Leu-His (Trt)-Lys(Boc)-Leu-Gln-Thr(tBu)-Tyr(tBu)-Pro-Arg(Pmc)-Thr(tBu)-AA'$_{25}$-AA'$_{26}$-Gly-AA'$_{28}$-Gly-Thr-Pro-ⓟ(SEQ. ID NO. 2)

wherein -ⓟ has the following formula with bridge group, internal structure and reticulate polymer:

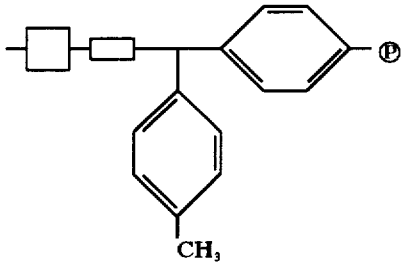

where ☐ is a bridge group,

▭ is an internal standard, and ⓟ is a reticulate polymer.

* * * * *

UNITED STATES PATENT AND TRADEMARK OFFICE
CERTIFICATE OF CORRECTION

PATENT NO. : 5,739,272
DATED : April 14, 1998
INVENTOR(S) : Canas Poblet, et al.

It is certified that error appears in the above-indentified patent and that said Letters Patent is hereby corrected as shown below:

On the title page, item [56], please add the following under REFERENCES CITED:

-- U.S. Patent Documents:

5,428,129    6/27/95    Ohsaki, et al.

Other Publications:

Florsheimer, et al. Peptides 1990, 21st European Peptide Symposium (1990) p. 131;

Wang, et al. J. Am. Chem. Soc. vol. 95 p. 1328 (1973); and

Harper's Review of Biochemistry, 20th Edition, 1985 p. 527.--

Signed and Sealed this

Seventeenth Day of November, 1998

*Attest:*

BRUCE LEHMAN

*Attesting Officer*    *Commissioner of Patents and Trademarks*